United States Patent
Smith, Jr. et al.

(10) Patent No.: US 6,232,509 B1
(45) Date of Patent: May 15, 2001

(54) ETHERIFICATION PROCESS

(75) Inventors: Lawrence A. Smith, Jr.; Henry J. Semerak; Willibrord A. Groten, all of Houston, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 12 days.

(21) Appl. No.: 09/591,520

(22) Filed: Jun. 9, 2000

Related U.S. Application Data

(63) Continuation of application No. 08/254,684, filed on Jun. 6, 1994, now abandoned.

(51) Int. Cl.[7] .............................. C07C 41/09; C07C 41/42
(52) U.S. Cl. ............................................ 568/697; 568/699
(58) Field of Search ...................................... 568/697, 699

(56) References Cited

U.S. PATENT DOCUMENTS

| | | | | |
|---|---|---|---|---|
| 4,504,687 | * | 3/1985 | Jones, Jr. | 568/697 |
| 5,248,837 | * | 9/1993 | Smith, Jr. et al. | 568/697 |

* cited by examiner

*Primary Examiner*—Rosalynd Keys
(74) *Attorney, Agent, or Firm*—Kenneth H. Johnson

(57) ABSTRACT

A process for the separation and recovery of methyl tertiary butyl ether from mixed $C_4/C_5$ streams, such as resulting from the co-production of methyl tertiary butyl ether and tertiary amyl methyl ether from the reaction of methanol with isobutene and isoamylenes in a mixed $C_4/C_5$ stream. In a distillation column reactor the reaction is carried out concurrently with distillation of the products from the unreacted materials. In the distillation little or no MTBE is carried overhead with the unreacted $C_4$'s, $C_5$'s and methanol by controlling the methanol concentration in said column to maintain substantially a methanol/$C_5$ azeotrope in the overheads.

17 Claims, 1 Drawing Sheet

ETHERIFICATION PROCESS

This is a continuation of application Ser. No. 08/254,684, filed Jun. 6, 1994 now abandoned.

BACKGROUND OF THE INVENTION

1. Field of the Invention

The present invention relates to the etherification of $C_4$ and $C_5$ isoolefins, with an alcohol such as methanol, to produce the corresponding tertiary ether. More particularly the invention relates to a process wherein a catalytic distillation process is used in the process and wherein both isobutene and isoamylene are contained in the charge and wherein methanol is used to produce methyl tertiary butyl ether (MTBE) and tertiary amyl methyl ether (TAME).

2. Related Information

The increased governmental restriction on gasoline has strained the availability of feed stocks for etherification. The use of the isoamylenes for the preparation of octane improvers for gasoline has increased. It is highly desirable to be able to employ mixed isobutene/isoamylene streams. In a conventional separation of the reaction components from the etherification of a mixed $C_4/C_5$ stream the separation of the unreacted $C_5$ components from the MTBE is quite difficult because of their close boiling points. Even small amounts of MTBE in the $C_5$ raffinate is detrimental to its use in a downstream gasoline alkylate plant.

U.S. Pat. No. 4,661,209 discloses the separation of MTBE from close boiling hydrocarbons by extractive distillation using a higher boiling oxygenated, nitrogenous and/or sulfur containing compound. The past necessity for such costly procedures has inhibited the actual feeding of $C_4$'s and $C_5$'s together to a reactor to co-produce MTBE and TAME. It has been found, however, that using a catalytic distillation system operated in a specific manner the separation can be achieved easily and concurrently in the reaction.

The reaction of an alcohol and an olefin and concurrent separation of the reactants from the reaction products by fractional distillation has been practiced for some time. The process is variously described in U.S. Pat. Nos. 4,232,177; 4,307,254; 4,336,407; 4,504,687; 4,987,807; and 5,118,873 all commonly assigned herewith. The isoolefins preferably react with the alcohol to form ethers. Briefly the alcohol and isoolefin are fed to a distillation column reactor having a distillation reaction zone containing a suitable catalyst, such as an acid cation exchange resin, in the form of catalytic distillation structure, and also having a distillation zone containing inert distillation structure.

U.S. Pat. No. 5,248,837 discloses a method for controlling catalytic distillation etherifications wherein the methanol concentration below the catalyst bed is controlled to a point that maximizes ether production and prevents alcohol from leaving with the bottoms ether produce. The patent discloses only the reaction of one isoolefin and one alcohol at a time. In particular the invention is embodied by the production of TAME by the reaction of methanol and isoamylene.

Commonly assigned patent application Ser. No. 08/120,644 discloses a similar process to U.S. Pat. No. 5,248,837 wherein the alcohol content is controlled by total oxygen in the form of OH. This system is particularly useful when a mixture of alcohols is used.

Neither U.S. Pat. No. 5,248,837 nor application Ser. No. 08/120,644 address the problem of separation of MTBE from the unreacted overheads containing the unreacted $C_5$'s.

It is an advantage of the present invention that MTBE product can be separated from the reactants when charging a mixed $C_4/C_5$ stream to produce MTBE and TAME.

SUMMARY OF THE INVENTION

Briefly, the present invention is the discovery that control of the methanol concentration in a mixture of $C_4$'s, $C_5$'s, and MTBE (or MTBE and TAME) in a distillation column, preferably a distillation column reactor where the ethers are co-produced, to maintain substantially an azeotrope of methanol and $C_5$ in the distillate allows for the separation of MTBE (or MTBE and TAME) from the unreacted $C_5$'s by fractionation. The separation is made possible because it has been found surprisingly that it is substantially easier to separate MTBE from the $C_5$/methanol azeotrope than it is to separate MTBE from $C_5$ hydrocarbons alone. The catalytic distillation column may be used alone or more desirably combined with a front end straight pass reactor. The upper limit on the $C_4$ content is determined by economics. Isobutene is a better reactant than isoamylene in this reaction, however, if the intent of the process is to react isoamylene then isoamylene should be maximized.

A preferred embodiment is the process for the co-production of MTBE and TAME from the reaction of the isobutene and isoamylenes contained in a mixed $C_4/C_5$ stream comprises the steps of:

(a) feeding methanol and a mixture comprising $C_5$ hydrocarbons including pentanes, n-pentenes and isoamylenes and $C_4$ hydrocarbons including butanes, n-butenes and isobutene to a down flow fixed bed straight pass reactor preferably at least 15 mole % substantially inert $C_4$ hydrocarbons including butanes and isobutene;

(b) reacting a portion of said isobutene and said isoamylene with a portion of said methanol in said down flow fixed bed reactor to form a first mixture containing methyl tertiary butyl ether, tertiary amyl methyl ether, unreacted methanol, isobutene, isoamylenes, unreacted $C_4$'s and unreacted $C_5$'s;

(c) feeding said first reaction mixture to a distillation column reactor;

(d) concurrently in said distillation column reactor
  (i) reacting a substantial portion of the said unreacted isobutene and said unreacted isoamylenes with unreacted methanol to form additional methyl tertiary butyl ether and tertiary amyl methyl ether in a second reaction mixture containing methyl tertiary butyl ether, tertiary amyl methyl ether and unreacted methanol, and
  (ii) separating said methyl tertiary butyl ether and said tertiary amyl methyl ether contained in said second reaction mixture from said unreacted $C_4$'s, unreacted $C_5$'s and unreacted methanol contained in said second reaction mixture by fractional distillation;

(e) removing said unreacted methanol, $C_4$'s and $C_5$'s from said distillation column reactor as overheads;

(f) controlling the methanol concentration in said column to maintain substantially a methanol/$C_5$ azeotrope in said overheads, (g) removing said methyl tertiary butyl ether and said tertiary amyl methyl ether from said distillation column as bottoms; and (h) condensing a portion of said overheads and returning a portion of said condensed overheads to said distillation column reactor as reflux.

Surprisingly it has been found that when the methanol concentration profile is appropriately controlled to allow only an azeotrope amount of methanol overhead the separation of the MTBE from the $C_5$'s is facilitated and methanol does not exit in the bottoms ether products.

In the etherification reaction, especially the TAME reaction, the presence of an excess of methanol is necessary to direct the otherwise reversible reaction toward the ether.

The reflux ratio may be adjusted to optimize the effect described above, preferably in range of 1:2 to 2:1.

DESCRIPTION OF THE PREFERRED EMBODIMENT

Figure 1:
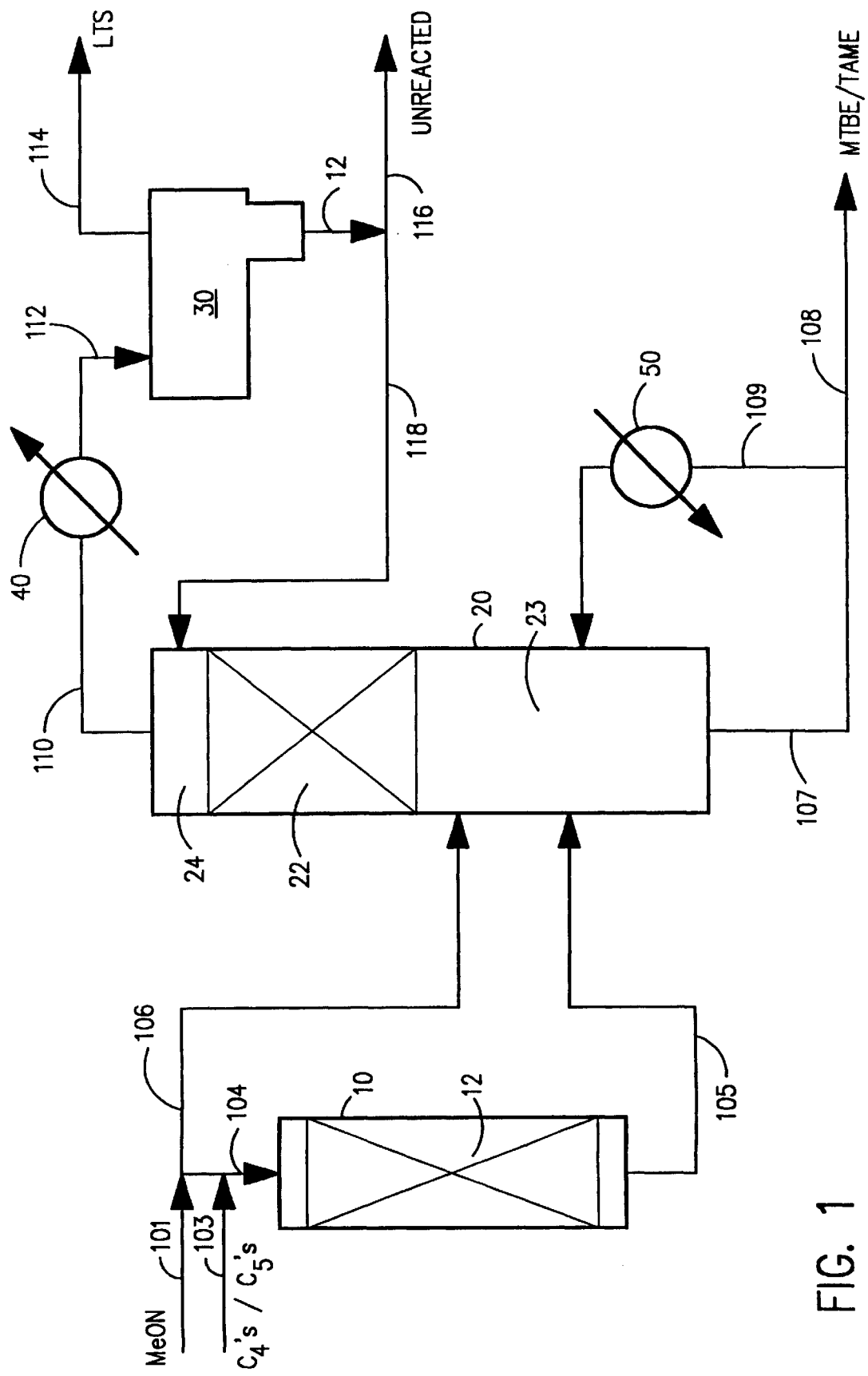
FIG. 1 is simplified flow diagram of one embodiment of the invention.

U.S. Pat. Nos. 5,003,124 and 4,950,803 disclose a liquid phase process for the etherification of $C_4$ or $C_5$ isoolefins with $C_1$ to $C_6$ alcohols in a boiling point fixed bed reactor that is controlled at a pressure to maintain the reaction mixture at its boiling point which may be directly attached to a catalytic distillation reactor.

As noted above in the etherification of olefins with an alcohol there is preferably an excess of the alcohol available in the reactor. This means that there is an excess of methanol in the reaction distillation zone of the distillation column reactor. In the distillation column reactor the methanol forms a minimum boiling azeotrope with either of the olefins. In the case where $C_4$ components are present the azeotrope is only slightly more volatile than the $C_4$'s alone, and therefore the methanol tends to remain in a relatively constant concentration with the $C_4$'s throughout the column. The concentration of the methanol in the $C_4$ azeotrope is about 4% (depending upon the composition of the $C_4$ mixture and operating pressure of the column), and it is necessary to operate with a methanol concentration to satisfy this azeotrope before the $C_5$ azeotrope can be satisfied.

In the case of the $C_5$'s, the azeotrope contains about 12 wt % methanol, and the boiling point of the azeotrope is 10 to 15 degrees F. below that of the corresponding $C_5$'s but above the $C_4$ and $C_4$/methanol azeotrope Thus, if the net flow of methanol into the column (allowing for that reacting in the column) is less than the azeotrope concentration in the distillate, the methanol concentration in the reaction distillation zone will be relatively quite low, about 1%. If the net methanol flow into the column is higher than the azeotrope, the methanol concentration will increase (60% has been measured) until methanol leaves with the TAME bottoms product. Neither case is desirable, because at low concentrations the conversion of isoamylene to TAME is low, whereas at high concentrations the TAME purity is affected by the presence of the excess methanol. Thus careful control of the methanol feed to keep just the azeotrope is necessary to obtain the most benefit from the present invention.

In one embodiment of the etherification of $iC_4^=$'s and $iC_5^=$'s, the olefin and an excess of methanol are first fed to a fixed bed reactor wherein most of the olefin is reacted to form the corresponding ether, methyl tertiary butyl ether (MTBE) and tertiary amyl methyl ether (TAME). The fixed bed reactor is operated at a given pressure such that the reaction mixture is at the boiling point, thereby removing the exothermic heat of reaction by vaporization of the mixture. The fixed bed reactor and process are described more completely in U.S. Pat. No. 4,950,803 which is hereby incorporated by reference.

The effluent from the fixed bed reactor is then fed to the distillation column reactor wherein the remainder of the $iC_4^=$'s or $iC_5^=$'s are converted to the ether and the methanol is separated from the ether which is withdrawn as bottoms. The $C_4$ or $C_5$ olefin stream generally contains only about 10 to 60 percent olefin, the remainder being inerts which are removed in the overheads from the distillation column reactor.

The catalytic distillation process employs a catalyst system (See U.S. Pat. Nos. 4,215,011 and 4,302,356) which provides for both reaction and distillation concurrently in the same reactor, at least in part within the catalyst system. The method involved is briefly described as one where concurrent reaction and distillation occur in combination reaction-distillation structures which are described in several U.S. patents, namely U.S. Pat. Nos. 4,242,530; 4,250,052; 4,232,177; 4,302,356; 4,307,254; and 4,336,407. Additionally U.S. Pat. Nos. 4,302,356 and 4,443,559 disclose catalyst structures which are useful as distillation structures.

Hydrocarbon feeds contemplated for this process may comprise:

| COMPONENT | MOLE % RANGE BROAD | PREFERRED |
|---|---|---|
| $C_5$'s | 15–85 | 40–70 |
| ISOAMYLENE | 5–30 | 15–25 |
| $C_4$'s | 15–85 | 40–60 |
| ISOBUTENE | 5–35 | 10–20 |
| $C_3$ AND LIGHTER | 0–10 | <5% |
| $C_6$ AND HEAVIER | 0–10 | <5% |

Catalysts preferred for the etherification process are acidic ion exchangers, which contain sulfonic acid groups, and which have been obtained by polymerization or copolymerization of aromatic vinyl compounds followed by sulfonation.

The resulting products preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Patent specification 908,247).

The ion exchange resin is preferably used in a granular size of about 0.25 to 1 mm, although particles from 0.15 mm up to about 1 mm may be employed.

The resin catalyst is loaded into the fixed bed reactor as a fixed bed of the granules. The feed to the reaction is fed to the bed in liquid phase. The bed may be horizontal, vertical or angled. Preferably the bed is vertical with the feed passing downward through the bed and exiting, after reaction, through the lower end of the reactor.

A preferred catalytic distillation structure for use herein comprises placing the acidic cation exchange resin particles into a plurality of pockets in a cloth belt, which is supported in the distillation column reactor by open mesh knitted stainless steel wire by twisting the two together in a helical form. This allows the requisite flows and prevents loss of catalyst. The cloth may be any material which is inert in the reaction. Cotton or linen are useful, but fiber glass cloth or "Teflon" cloth are preferred. The catalytic distillation structure when loaded into the column constitutes a distillation reaction zone.

FIG. 1 presents a simplified flow diagram of the process. A mixed stream of $C_4$'s and $C_5$'s containing isobutene and isoamylenes are fed via line 103 and methanol is fed via line 101. The methanol and mixed $C_4/C_5$ stream are combined in flow line 104 and fed to the down flow fixed bed reactor 10 (guard bed) which contains a fixed bed 12 of the acid cation exchange resin. The pressure of reactor 10 is controlled such that the mixture within the reactor is at its boiling point. The exothermic heat of reaction is absorbed as latent heat of vaporization controlling the temperature in the reactor. In the reactor 10 most of the isobutene is reacted with methanol to form the MTBE while only about half of the isoamylene is converted to TAME.

The effluent from the down flow fixed bed reactor containing MTBE, TAME, methanol, unreacted $C_4$'s an $C_5$'s is removed via line 105 and fed into the lower portion 23 of a distillation column reactor 20. The lower portion 23 of the distillation column reactor contains standard distillation structure such as inert packing, sieve trays or bubble cap trays. In this section, the distillation section, the MTBE and TAME are recovered and taken as bottoms via line 107. Heat may be added as necessary to the distillation column reactor via circulation of bottoms through flow line 109 and reboiler 50.

The upper portion of the distillation column reactor contains the catalytic distillation structure in the distillation reaction zone 22. Additional conventional distillation structure 24 may be placed above the distillation reaction zone 22. The unreacted methanol, $C_4$'s and $C_5$'s are boiled up into the distillation reaction zone 22 where most of the remainder of the isobutene and isoamylenes are converted to MTBE and TAME which are simultaneously distilled down into distillation zone 23 and finally removed as product. Unreacted methanol, $C_4$'s, $C_5$'s and inerts are taken overhead via flow line 110 and passed through partial condenser 40 where all of the condensible materials are condensed and collected in receiver 30. Uncondensible lights are removed from receiver 30 via line 114 while the liquid is removed via line 120. Overhead product, mostly unreacted inert $C_4$'s, $C_5$'s and methanol, is removed via line 116. A portion of the liquid overheads is returned to the distillation column reactor as reflux via line 118.

If desired, methanol can be added directly to the distillation column reactor via line 106 to control the methanol concentration within the distillation column reactor at the optimum to satisfy the $C_4$ and $C_5$/methanol azeotropes and the reaction requirements.

Surprisingly it has been found that when sufficient methanol is fed to the column to maintain the methanol concentration below the catalytic reaction zone constant, the separation of the MTBE from the hydrocarbons is achieved.

EXAMPLES

In the following examples the mixed $C_4/C_5$ stream and methanol is first fed to a 3" diameter single pass downflow fixed bed reactor containing 9,500 grams of catalyst for case 1 and 2 and 9,400 grams of catalyst for case 3 and 4. The effluent from the reactor is then fed to a 3" diameter distillation column reactor having 30 feet of the same catalyst in the form of distillation structure as described above in the middle 30 feet of the tower. There are 20 feet of inert packing above and 50 feet of inert packing below the catalyst. The flows and conditions are varied as shown in TABLE I. The methanol concentration was measured directly below the catalyst at what is termed the mid reflux. The results are shown in the TABLE. While there was essentially no MTBE in the overheads in any of cases, Case 6 shows the result of running with too much methanol in the mid reflux, i.e., methanol exits with the bottoms in substantial quantities.

While the concentration methanol is measured and controlled in the mid reflux it could also be measured and controlled at any point below the bed. In some operations there is no methanol in the bottoms, e.g. cases 3 and 4. Conversions of isobutene and isoamylenes in the guard bed reactor of about 95 and 55 mole % respectively are shown in cases 1, 2, 5 and 6 with case 1 illustrating about 100% overall conversion.

TABLE I

| | Case | | | | | |
|---|---|---|---|---|---|---|
| | 1 | 2 | 3 | 4 | 5 | 6 |
| Conditions Temp. ° F. | | | | | | |
| BTMS | 282 | 292 | 300 | 300 | 284 | 246 |
| AVG Cat bed | 169 | 165 | 172 | 172 | 160 | 155 |
| Flow Rate, lbs/hr | | | | | | |
| $C_4$'s | 32.5 | 21.9 | 57.0 | 57.0 | 32.5 | 32.1 |
| $C_5$'s | 31.8 | 43.0 | 46.1 | 46.1 | 26.8 | 26.8 |
| Prim MeOH | 9.0 | 10.0 | 15.8 | 15.8 | 9.5 | 9.5 |
| Sec. MeOH | 0.0 | 0.0 | 1.7 | 1.6 | 0.0 | 1.0 |
| Reflux | 60.0 | 85.0 | 101.5 | 75.0 | 35.0 | 44.3 |
| $C_5$'s to Storage | 57.4 | 59.6 | 87.0 | 87.0 | 60.0 | 60.0 |
| Btms | 14.8 | 14.8 | 33.6 | 33.5 | 14.9 | 14.5 |
| Mid Reflux Composition, % (liquids below the catalyst and above the column exit) | | | | | | |
| MeOH | 0.750 | 1.042 | 4.000 | 3.882 | 1.657 | 11.84 |
| MTBE | 0.571 | 1.328 | 0.837 | 2.340 | 1.786 | 0.537 |
| TAME | 5.079 | 4.078 | 2.057 | 3.450 | 6.931 | 5.788 |
| Overheads Composition, % | | | | | | |
| MeOH | 7.00 | 9.18 | 8.00 | 8.00 | 6.89 | 7.10 |
| MTBE | 0.00 | 0.00 | 0.00 | 0.00 | 0.02 | 0.27 |
| TAME | 0.00 | 0.00 | 0.00 | 0.00 | 0.08 | 0.01 |

TABLE I-continued

|  | Case | | | | | |
|---|---|---|---|---|---|---|
|  | 1 | 2 | 3 | 4 | 5 | 6 |
| Bottoms Composition, % | | | | | | |
| MeOH | 0.03 | 1.07 | 0.00 | 0.00 | 0.12 | 7.36 |
| MTBE | 29.18 | 21.83 | 39.00 | 40.00 | 32.71 | 29.1 |
| TAME | 67.22 | 79.74 | 57.50 | 55.50 | 60.81 | 57.8 |
| Conversion $C_4^-/C_5^-$ | | | | | | |
| Guard Bed | 96.6/54.4 | 96.8/56.9 | 70.0/25.0 | 70.0/25.0 | 96.4/58.1 | 97.5/59.1 |
| Column | 43.3/92.4 | 0.0/80.3 | 97.0/93.0 | 93.0/97.0 | 13.1/75.4 | 70.7/74.5 |
| Overall | 98.1/96.5 | 95.8/91.5 | 99.1/94.8 | 97.0/90.3 | 96.9/89.7 | 99.3/89.6 |

The invention claimed is:

1. A process for the co-production of MTBE and TAME from the reaction of the isobutene and isoamylenes contained in a mixed $C_4/C_5$ stream comprising the steps of:

feeding methanol and a mixture comprising $C_4/C_5$ hydrocarbons including isobutene, pentanes and isoamylenes to a distillation column reactor;

concurrently in said distillation column reactor
 (i) reacting a portion of the said isobutene and said isoamylenes with said methanol to form methyl tertiary butyl ether and tertiary amyl methyl ether in a reaction mixture containing methyl tertiary butyl ether, tertiary amyl methyl ether, unreacted $C_4$'s, unreacted $C_5$'s and unreacted methanol, and
 (ii) separating said methyl tertiary butyl ether and said tertiary amyl methyl ether contained in said reaction mixture from said unreacted $C_4$'s, unreacted $C_5$'s and unreacted methanol contained in said reaction mixture by fractional distillation;

removing said unreacted methanol, $C_4$'s and $C_5$'s from said distillation column reactor as overheads;

controlling the methanol concentration in said column to maintain substantially a methanol/$C_5$ azeotrope in said overheads, removing said methyl tertiary butyl ether and said tertiary amyl methyl ether from said distillation column as bottoms.

2. The process according to claim 1 wherein methyl tertiary butyl ether and tertiary amyl methyl ether are present in said feed.

3. The process according to claim 2 wherein substantially no methanol exits the column in the bottoms.

4. A process for the co-production of MTBE and TAME from the reaction of the isobutene and isoamylenes contained in a mixed $C_4/C_5$ stream comprising the steps of:

feeding methanol and a mixture comprising $C_5$ hydrocarbons including pentanes and isoamylenes and at least 15% mole percent substantially inert $C_4$ hydrocarbons including butanes and isobutene to a down flow fixed bed reactor;

reacting a portion of said isobutene and said isoamylene with a portion of said methanol in said down flow fixed bed reactor to form a first mixture containing methyl tertiary butyl ether, tertiary amyl methyl ether, unreacted methanol, isobutene, isoamylenes, unreacted $C_4$'s and unreacted $C_5$'s;

feeding said first reaction mixture to a distillation column reactor;

concurrently in said distillation column reactor
 (i) reacting a substantial portion of the said unreacted isobutene and said unreacted isoamylenes with unreacted methanol to form additional methyl tertiary butyl ether and tertiary amyl methyl ether in a second reaction mixture containing methyl tertiary butyl ether, tertiary amyl methyl ether, unreacted $C_4$'s, unreacted $C_5$'s and unreacted methanol, and
 (ii) separating said methyl tertiary butyl ether and said tertiary amyl methyl ether contained in said second reaction mixture from said unreacted $C_4$'s, unreacted $C_5$'s and unreacted methanol contained in said second reaction mixture by fractional distillation;

removing said unreacted methanol, $C_4$'s and $C_5$'s from said distillation column reactor as overheads;

controlling the methanol concentration in said column to maintain substantially a methanol/$C_5$ azeotrope in said overheads, removing said methyl tertiary butyl ether and said tertiary amyl methyl ether from said distillation column as bottoms; and condensing a portion of said overheads and returning a portion of said condensed overheads to said distillation column reactor as reflux.

5. The process according to claim 4 wherein the conversion of said isobutenes and said isoamylenes in said down flow fixed bed reactor is about 95 and 55 mole % respectively.

6. The process according to claim 5 wherein the overall conversions of both isobutene and isoamylenes is about 100 mole %.

7. The process according to claim 4 wherein said reflux to distillate ratio is controlled between 0.5 and 2.0.

8. The process according to claim 4 wherein the methanol concentration directly below the catalyst bed is controlled at a desired concentration to maintain a sufficient methanol concentration in the catalyst bed to satisfy the $C_4$ and $C_5$ azeotropes present and to support the reaction.

9. The process according to claim 8 wherein a stream containing methanol is fed to said distillation column reactor to control said methanol concentration.

10. The process according to claim 8 wherein there is substantially no methanol in said bottoms.

11. The process according to claim 4 wherein $C_4$'s comprise 15–85 mole % in said first stream.

12. A method for the separation of MTBE from a reaction mixture containing methyl tertiary butyl ether, tertiary amyl methyl ether, unreacted $C_4$'s, unreacted $C_5$'s and unreacted methanol comprising the steps of:

feeding to a distillation column a reaction mixture containing methyl tertiary butyl ether, unreacted $C_4$'s, unreacted $C_5$'s and unreacted methanol;

removing said unreacted methanol, $C_4$'s and $C_5$'s from said distillation column as overheads;

controlling the methanol concentration in said column to maintain substantially a methanol/$C_5$ azeotrope in said overheads, removing said methyl tertiary butyl ether from said distillation column as bottoms.

13. A method for the separation of MTBE and TAME from a reaction mixture containing methyl tertiary butyl ether, unreacted $C_4$'s, unreacted $C_5$'s and unreacted methanol comprising the steps of:

feeding to a distillation column a reaction mixture containing methyl tertiary butyl ether, unreacted $C_4$'s, unreacted $C_5$'s and unreacted methanol;

removing said unreacted methanol, $C_4$'s and $C_5$'s from said distillation column as overheads;

controlling the methanol concentration in said column to maintain substantially a methanol/$C_5$ azeotrope in said overheads;

removing said methyl tertiary butyl ether from said distillation column as bottoms.

14. A process for the co-production of MTBE and TAME from the reaction of the isobutene and isoamylenes contained in a mixed $C_4/C_5$ stream comprising the steps of:

feeding methanol and a mixture comprising $C_4/C_5$ hydrocarbons including isobutene, pentanes and isoamylenes to a distillation column reactor;

concurrently in said distillation column reactor
(i) reacting a portion of the said isobutene and said isoamylenes with said methanol to form methyl tertiary butyl ether and tertiary amyl methyl ether in a reaction mixture containing methyl tertiary butyl ether, tertiary amyl methyl ether, unreacted $C_4$'s, unreacted $C_5$'s and unreacted methanol, and
(ii) separating said methyl tertiary butyl ether and said tertiary amyl methyl ether contained in said reaction mixture from said unreacted $C_4$'s, unreacted $C_5$'s and unreacted methanol contained in said reaction mixture by fractional distillation;

removing said unreacted methanol, $C_4$'s and $C_5$'s from said distillation column reactor as overheads;

removing said methyl tertiary butyl ether and said tertiary amyl methyl ether from said distillation column as bottoms; and controlling the methanol concentration in said column to maintain substantially a methanol/$C_5$ azeotrope such that substantially all of the methanol is removed as overheads and substantially all of the methyl tertiary butyl ether is removed as bottoms.

15. A process for the co-production of MTBE and TAME from the reaction of the isobutene and isoamylenes contained in a mixed $C_4/C_5$ stream comprising the steps of:

feeding methanol and a mixture comprising $C_5$ hydrocarbons including pentanes and isoamylenes and at least 15% mole percent substantially inert $C_4$ hydrocarbons including butanes and isobutene to a down flow fixed bed reactor;

reacting a portion of said isobutene and said isoamylene with a portion of said methanol in said down flow fixed bed reactor to form a first mixture containing methyl tertiary butyl ether, tertiary amyl methyl ether, unreacted methanol, isobutene, isoamylenes, unreacted $C_4$'s and unreacted $C_5$'s;

feeding said first reaction mixture to a distillation column reactor;

concurrently in said distillation column reactor
(i) reacting a substantial portion of the said unreacted isobutene and said unreacted isoamylenes with unreacted methanol to form additional methyl tertiary butyl ether and tertiary amyl methyl ether in a second reaction mixture containing methyl tertiary butyl ether, tertiary amyl methyl ether, unreacted $C_4$'s, unreacted $C_5$'s and unreacted methanol, and
(ii) separating said methyl tertiary butyl ether and said tertiary amyl methyl ether contained in said second reaction mixture from said unreacted $C_4$'s, unreacted $C_5$'s and unreacted methanol contained in said second reaction mixture by fractional distillation;

removing said unreacted methanol, $C_4$'s and $C_5$'s from said distillation column reactor as overheads;

removing said methyl tertiary butyl ether and said tertiary amyl methyl ether from said distillation column as bottoms; and condensing a portion of said overheads and returning a portion of said condensed overheads to said distillation column reactor as reflux; and controlling the methanol concentration in said column to maintain substantially a methanol/$C_5$ azeotrope such that substantially all of the methanol is removed as overheads and substantially all of the methyl tertiary butyl ether is removed as bottoms.

16. A method for the separation of MTBE from a reaction mixture containing methyl tertiary butyl ether, tertiary amyl methyl ether, unreacted $C_4$'s, unreacted $C_5$'s and unreacted methanol comprising the steps of:

feeding to a distillation column a reaction mixture containing methyl tertiary butyl ether, unreacted $C_4$'s, unreacted $C_5$'s and unreacted methanol;

removing said unreacted methanol, $C_4$'s and $C_5$'s from said distillation column as overheads;

removing said methyl tertiary butyl ether from said distillation column as bottoms; and controlling the methanol concentration in said column to maintain substantially a methanol/$C_5$ azeotrope such that substantially all of the methanol is removed as overheads and substantially all of the methyl tertiary butyl ether is removed as bottoms.

17. A method for the separation of MTBE and TAME from a reaction mixture containing methyl tertiary butyl ether, unreacted $C_4$'s, unreacted $C_5$'s and unreacted methanol comprising the steps of:

feeding to a distillation column a reaction mixture containing methyl tertiary butyl ether, unreacted $C_4$'s, unreacted $C_5$'s and unreacted methanol;

removing said unreacted methanol, $C_4$'s and $C_5$'s from said distillation column as overheads;

controlling the methanol concentration in said column to maintain substantially a methanol/$C_5$ azeotrope;

removing substantially all of said methyl tertiary butyl ether from said distillation column as bottoms; and removing substantially all of said methanol from said distillation column in said overheads.

* * * * *